(12) United States Patent
Murase

(10) Patent No.: US 9,259,151 B2
(45) Date of Patent: Feb. 16, 2016

(54) OPHTHALMIC IMAGING APPARATUS

(71) Applicant: NIDEK CO., LTD., Gamagori, Aichi (JP)

(72) Inventor: Yuji Murase, Aichi (JP)

(73) Assignee: NIDEK CO., LTD., Aichi (JP)

( * ) Notice: Subject to any disclaimer, the term of this patent is extended or adjusted under 35 U.S.C. 154(b) by 123 days.

(21) Appl. No.: 14/161,733

(22) Filed: Jan. 23, 2014

(65) Prior Publication Data

US 2014/0204341 A1      Jul. 24, 2014

(30) Foreign Application Priority Data

Jan. 23, 2013   (JP) .................................. 2013-010643

(51) Int. Cl.
*A61B 3/14* (2006.01)
*A61B 3/10* (2006.01)
*A61B 3/12* (2006.01)

(52) U.S. Cl.
CPC ............... *A61B 3/102* (2013.01); *A61B 3/1025* (2013.01); *A61B 3/1233* (2013.01)

(58) Field of Classification Search
CPC ........ A61B 3/102; A61B 3/1025; A61B 3/12; A61B 3/1233; A61B 3/14
USPC .......................... 351/205, 206, 208, 210, 246
See application file for complete search history.

(56) References Cited

U.S. PATENT DOCUMENTS

| 2010/0110171 A1 | 5/2010 | Satake |
| 2013/0229622 A1 | 9/2013 | Murase et al. |
| 2014/0009738 A1* | 1/2014 | Satake et al. .................. 351/206 |
| 2014/0211155 A1* | 7/2014 | Sakagawa et al. ............ 351/206 |

FOREIGN PATENT DOCUMENTS

| JP | 2010-110392 A | 5/2010 |
| JP | 2013-180127 A | 9/2013 |

* cited by examiner

*Primary Examiner* — Huy K Mai
(74) *Attorney, Agent, or Firm* — Sughrue Mion, PLLC

(57) ABSTRACT

There is provided an ophthalmic imaging apparatus including an optical coherence tomography (OCT) optical system for acquiring a tomographic image of a subject eye, an observation optical system configured to acquire a front image of the subject eye. The apparatus functions as an image generation unit which repeatedly generates the tomographic image based on an output signal from the OCT optical system, and repeatedly generates the front image based on an output signal from the observation optical system, a determination unit which detects a positional deviation between a reference front image and each of front images generated by the image generation unit, and determines consecutiveness of the front images whose positional deviation satisfies a permissible range, and a selection process unit which selects one of multiple tomographic images generated by the image generation unit, based on a determination result by the determination unit.

10 Claims, 3 Drawing Sheets

OPHTHALMIC IMAGING APPARATUS

CROSS-REFERENCE TO RELATED APPLICATION

This application claims priority from Japanese Patent Application No. 2013-010643, filed on Jan. 23, 2013, the entire subject matter of which is incorporated herein by reference.

TECHNICAL FIELD

The present disclosure relates to an ophthalmic imaging apparatus which takes an optical tomographic image of an eye.

BACKGROUND

There has been known an ophthalmic imaging apparatus which takes an optical tomographic image of an eye by using an optical coherence tomography (OCT) device. For example, this apparatus controls an optical scanner to scan an eye fundus by using a measurement light, and acquires the tomographic image of the eye (for example, tomographic image of the eye fundus). Then, the acquired tomographic image is used in evaluating a state of the eye (refer to JP-A-2010-110392).

In order to average noise components included in the tomographic image, the apparatus acquires multiple tomographic images and calculates an averaged image based on those multiple images. For example, the averaged image is acquired by adding a luminance value in each pixel relating to a substantially identical region in the multiple tomographic images and obtaining an average value thereof.

Incidentally, when acquiring a tomographic image with respect to a transverse position set in advance, a subject eye might move in some cases. In those cases, the tomographic image would be acquired with respect to a position different from the position set in advance.

For example, when acquiring an averaged image, if a template tomographic image serving as a reference is acquired at a deviated position, an appropriate averaged image cannot be acquired.

SUMMARY

According to an illustrative embodiment of the present disclosure, there is provided an ophthalmic imaging apparatus comprising:
  an optical coherence tomography (OCT) optical system configured to acquire a tomographic image of a subject eye by using interference between a measurement light which is emitted to the subject eye and a reference light;
  an observation optical system configured to acquire a front image of the subject eye;
  a processor; and
  a memory storing computer readable instructions, when executed by the processor, causing the ophthalmic imaging apparatus to function as:
    an image generation unit configured to repeatedly generate the tomographic image based on an output signal from the OCT optical system, and repeatedly generate the front image based on an output signal from the observation optical system;
    a determination unit configured to detect a positional deviation between a front image set as a reference front image and each of front images generated by the image generation unit, and to determine consecutiveness of the front images whose positional deviation satisfies a permissible range; and
    a selection process unit configured to perform selection process to select one of multiple tomographic images generated by the image generation unit, based on a determination result by the determination unit.

According to another illustrative embodiment of the present disclosure, there is provided an ophthalmic imaging apparatus comprising:
  an OCT optical system configured to acquire a tomographic image of a subject eye by using interference between a measurement light which is emitted to the subject eye and a reference light;
  an observation optical system configured to acquire a front image of the subject eye; and
  a controller configured to:
    repeatedly generate the tomographic image based on an output signal from the OCT optical system, and repeatedly generate the front image based on an output signal from the observation optical system;
    detect a positional deviation of each of multiple front images with respect to a reference front image, the multiple front images being consecutive in an acquisition order;
    select, as a reference tomographic image, a tomographic image acquired when the detected positional deviation consecutively satisfies a permissible range, and not select, as the reference tomographic image, a tomographic image acquired when the detected positional deviation does not satisfy the permissible range or when the positional deviation satisfying the permissible range is not consecutive; and
    synthesize the selected reference tomographic image and a tomographic image acquired at a time different from an acquisition time of the reference tomographic image.

BRIEF DESCRIPTION OF THE DRAWINGS

The above and other aspects of the present disclosure will become more apparent and more readily appreciated from the following description of illustrative embodiments of the present disclosure taken in conjunction with the attached drawings, in which.

DESCRIPTION OF ILLUSTRATIVE EMBODIMENTS

An illustrative embodiment of the present disclosure will be described with reference to the drawings. FIGS. 1 to 4 are views according to illustrative embodiments of the present disclosure.

<Overview>

Figure 1:
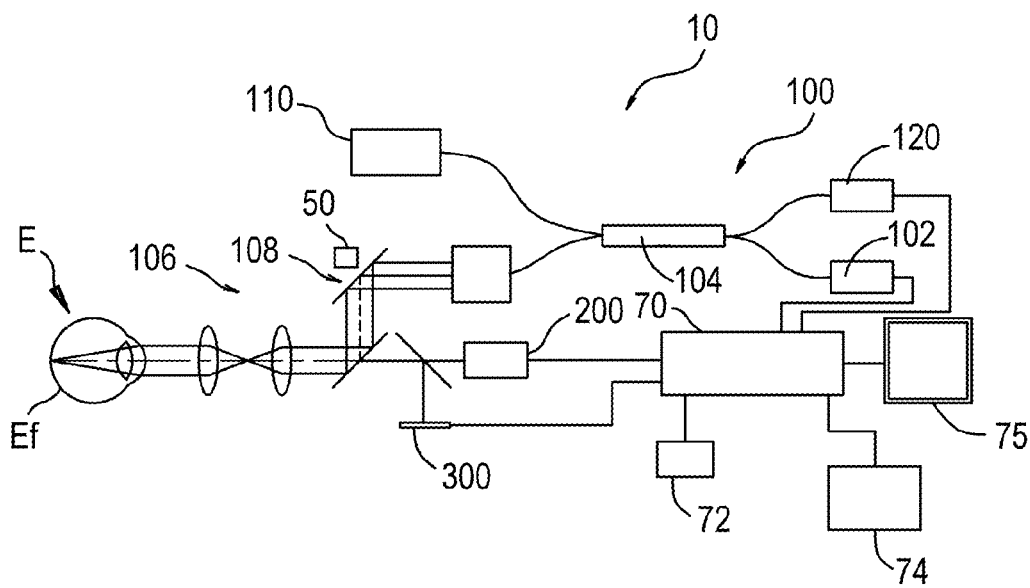
FIG. 1 is a schematic diagram showing a configuration of an ophthalmic imaging apparatus according to an example.

An ophthalmic imaging apparatus 10 mainly includes an OCT optical system 100, an observation optical system 200 and a control unit 70 (refer to FIG. 1). The OCT optical system 100 is configured to acquire a tomographic image of a subject eye using interference between a measurement light which is emitted to a subject eye and a reference light. The OCT optical system 100 may include an optical scanner 108. The optical scanner 108 is configured to scan the subject eye by using the measurement light emitted to the subject eye. The observation optical system 200 is configured to acquire a front image of the subject eye.

The control unit 70 operates, for example, as an image generation unit. The control unit 70 may repeatedly generate the tomography images based on an output signal from the OCT optical system 100, and may repeatedly generate the front image based on an output signal from the observation optical system 200. The tomographic image and the front image which are repeatedly generated are temporarily stored, for example, in a memory 74.

<Determination of Consecutiveness>

The control unit 70 operates, for example, as a consecutiveness determination unit. That is, the control unit 70 may detect a positional deviation between the front image set as a reference front image and each of the front images by image processing, and may determine consecutiveness of the front images whose positional deviation satisfies a permissible range. The reference front image may be, for example, the front image which is acquired when a start signal for acquiring an image is issued. Alternatively, the reference front image may be the front image which is used when setting a scanning position on a still image (for more details, refer to JP-A-2013-180127). The control unit 70 determines, for example, the consecutiveness of the front images which are generated by the image generation unit (control unit 70) and stored in the memory 74.

When determining the consecutiveness, the control unit 70 may determine whether the front images whose positional deviation with respect to the reference front image satisfies a permissible range are consecutive (for example, two times). The control unit 70 may determine whether the front images whose positional deviation with respect to the reference front image satisfies the permissible range are consecutive for three or more times.

Specifically, when determining the consecutiveness of the positional deviation, for example, the control unit 70 targets multiple front images which are consecutive in an acquisition order. As the front images which are consecutive in the acquisition order, for example, it can be considered to use the front images which are repeatedly acquired as a live image, that is, the front images which are consecutive on a frame by frame. For example, when multiple front images (which are consecutive in the acquisition order) consecutively satisfies the permissible range (for example, all), the control unit 70 considers that the multiple front images satisfying the permissible range are consecutive.

<Selection of Tomographic Image Using Consecutiveness Determination>

The control unit 70 operates, for example, as a selection process unit. That is, the control unit 70 may perform selection process on the tomographic image based on a determination result of consecutiveness. According to this configuration, for example, it is possible to properly select or discard the tomographic image based on the front images. The control unit 70 may select the tomographic image when it is determined that there is consecutiveness. The process of discarding the tomographic image when it is determined that there is no consecutiveness is one mode of the process of selecting the tomographic image when it is determined that there is consecutiveness. For example, the control unit 70 performs selection process on the tomographic image stored in the memory 74 by using the determination result of the consecutiveness. When discarding the tomographic images, the temporarily stored tomographic images may be deleted from the memory 74.

As the selection process, the control unit 70 may associate the determination result with the tomographic image acquired while acquiring a series of front images used in acquiring the determination result. The control unit 70 may distinguish each of the tomographic images by using the determination result. The control unit 70 may distinguish between the tomographic image acquired when the front images whose the positional deviation satisfies the permissible range are consecutive and the tomographic images acquired when the front images whose the positional deviation satisfies the permissible range are not consecutive.

<Application of Selection Process>

The control unit 70 operates, for example, as an image synthesis unit which synthesizes multiple acquired tomographic images. That is, the control unit 70 may select a reference tomographic image when synthesizing the images, from the repeatedly generated tomographic images based on the determination result of the consecutiveness. Then, the control unit 70 may synthesize the selected reference tomographic image and at least one tomographic image acquired at a time different from that of the reference tomographic image. Accordingly, for example, the tomographic image acquired for a proper position is set to be a reference image. Accordingly, it is possible to acquire an appropriate synthesized image.

As a method of image synthesizing, it can be employed a method of synthesizing multiple tomographic images acquired at the same scanning position set in advance. The synthesized image may be an averaged image, a super-resolution image, a blood flow measurement image obtaining a difference between the respective tomographic images, a synthesized image between a retinal tomographic image and a choroid tomographic image, a panoramic tomographic image, a functional OCT image obtaining a change in brightness between the tomographic images, and a polarization characteristic image where respective images of a first polarization component and a second polarization component are synthesized by PS-OCT.

The control unit 70 operates, for example, as a scanning control unit. That is, the control unit 70 may control the drive of the optical scanner 108 to scan the same scanning position set in advance multiple times by using the measurement light. The control unit 70 may select the tomographic image corresponding to the scanning position set in advance, based on the determination result of the consecutiveness. Accordingly, for example, it is possible to reliably acquire the tomographic image corresponding to the scanning position set in advance, from the tomographic images acquired by scanning the same scanning position.

In some cases, the scanning position may be changed from the initial scanning position due to movement of an eye. The control unit 70 may control the drive of the optical scanner 108, based on the front image acquired by the observation optical system 200, and may cause the optical scanner 108 to perform a correction operation (tracking operation) of the scanning position.

Further, the control unit 70 may control the drive of the optical scanner 108 to sequentially scan multiple scanning positions set by a scan pattern formed from multiple scanning lines, by using the measurement light. The control unit 70 may select the tomographic image corresponding to the scanning position, based on the determination result of the consecutiveness. Accordingly, for example, even when acquiring the tomographic image at multiple different transverse positions, it is possible to reliably acquire the tomographic image at the scanning position set in advance.

The control unit 70 may use the same reference front image when determining the consecutiveness used in selecting the tomographic image at a first transverse position and when determining the consecutiveness used in selecting the tomographic image at a second transverse position. Accordingly, a positional relationship between the respective transverse positions is ensured.

The selection process is not limited to the above-described method. That is, the selection process may also be used when acquiring the tomographic image at the same position as the transverse position where the tomographic image is acquired during the follow-up observation in the past. For example, the control unit 70 detects positional deviation between the front image (reference front image) which is acquired simultaneously with the tomographic image in the past and the front image which is acquired in real time on a different day. Then, the control unit 70 determines the consecutiveness of the positional deviation of the front images, and selects the tomographic image acquired in parallel with the front image used in acquiring the determination result. Further, the selection process may be used when selecting a tomographic image in a line imaging.

<Correspondence of Front Image and Tomographic Image>

The control unit 70 may select the tomographic image acquired while acquiring a series of front images which are determined to be consecutive, as the tomographic image acquired at a proper position. Accordingly, for example, it is possible to reliably select the tomographic image acquired at the proper position.

The control unit 70 operates, for example, as a specifying process unit which specifies the tomographic images acquired while acquiring a series of front images. That is, the control unit 70 may specify the tomographic images acquired while acquiring a series of front images, for example, by using a generation timing of the front image which is generated by the image generation unit (control unit 70).

The control unit 70 may specify the tomographic image acquired while acquiring a series of front images, based on control information when the observation optical system 200 is controlled. If the observation optical system 200 is an SLO optical system, for example, a drive position of the scanner can be considered as the control information.

Example

FIG. 1 is a schematic diagram showing a configuration of an ophthalmic imaging apparatus according to an example. In the following description, an eye fundus imaging apparatus which performs eye fundus imaging on a subject eye will be described as an example of the ophthalmic imaging apparatus. Of course, the ophthalmic imaging apparatus is not limited to the eye fundus imaging apparatus, and includes an anterior ocular segment imaging apparatus which performs anterior ocular segment imaging on a subject eye.

Referring to FIG. 1, a schematic configuration of an ophthalmic imaging apparatus 10 according to the present example will be described. The ophthalmic imaging apparatus 10 mainly includes the OCT optical system 100, the observation optical system 200, an ocular fixation target projection unit 300 and the control unit 70.

<OCT Optical System>

The OCT optical system 100 is an interference optical system for acquiring a tomographic image of a tissue (for example, an eye fundus Ef) of a subject eye E, and includes an optical coherence tomography (OCT) device. Specifically, the OCT optical system 100 mainly includes a measurement light source 102, a coupler (light divider) 104, a measurement optical system 106, a reference optical system 110 and a detector (light receiving element) 120.

Specifically, the coupler (light divider) 104 divides a light emitted from the measurement light source 102 into an optical path of the measurement optical system 106 and an optical path of the reference optical system 110. The measurement optical system 106 guides a measurement light to the eye fundus Ef of the eye E. The reference optical system 110 generates a reference light. The OCT optical system 100 synthesizes the measurement light reflected on the eye fundus Ef with the reference light. The detector 120 (light receiving element) receives the synthesized light.

The OCT optical system 100 includes a light emitting position change unit (for example, the optical scanner 108 and the ocular fixation target projection unit 300) that changes a light emitting position of the measurement light on the eye fundus Ef, in order to change an imaging position on the eye fundus EF. The control unit 70 controls an operation of the light emitting position change unit, based on set imaging position information, and acquires the tomographic image based on a light receiving signal from the detector 120.

The detector 120 (light receiving element) detects an interference state between the measurement light and the reference light. In a case of a Fourier-domain OCT, spectral intensity of interference light is detected by the detector 120, and a depth profile (A scan signal) is acquired in a predetermined range by performing Fourier transformation on spectral intensity data. The ophthalmic imaging apparatus 10 can employ various OCTs. For example, the ophthalmic imaging apparatus 10 may employ any one of a spectral-domain OCT (SD-OCT), a swept-source OCT (SS-OCT) and a time-domain OCT (TD-OCT).

The optical scanner 108 scans the eye fundus of the subject eye by using the light emitted from the measurement light source. For example, the scanner 108 scans the eye fundus two-dimensionally (in an XY direction (a transverse direction)) by using the measurement light. The optical scanner 108 is arranged at a substantially conjugating position with the pupil of the eye. The optical scanner 108 is for example, configured to have two galvanometer mirrors, and a reflection angle thereof is arbitrarily adjusted by a drive mechanism 50.

That is, a light flux emitted from the measurement light source 102 is caused to change its reflection (traveling) direction, and scans the eye fundus in an arbitrary direction. Accordingly, the imaging position on the eye fundus Ef is changed. The optical scanner 108 may employ any configuration which causes the light to be deflected. For example, in addition to a reflection mirror (a galvanometer mirror, a polygon mirror and a resonant scanner), an acousto-optical modulator (AOM) which changes the traveling (deflection) direction of the light may be used.

The reference optical system 110 generates the reference light. As described above, the reference light is synthesized with a reflection light acquired by the reflection of the measurement light on the eye fundus Ef. The reference optical system 110 may be a Michelson type or a Mach-Zehnder type. The reference optical system 110 is, for example, configured from a reflection optical system (for example, a reference mirror). The light from the coupler 104 is reflected by the reflection optical system. Accordingly, the light is caused to return to the coupler 104 again, and is guided to the detector 120. As another example, the reference optical system 110 is formed from a transmission optical system (for example, an optical fiber). The light from the coupler 104 is not caused to return to the coupler 104, but is transmitted therethrough, so that the light is guided to the detector 120.

The reference optical system 110 has a configuration for changing a difference in the length of the optical paths of the measurement light and the reference light by moving an optical member in the optical path for the reference light. For example, the reference mirror is moved in an optical axis direction. The configuration for changing the difference in the length of the optical paths may be arranged in the optical path of the measurement light of the measurement optical system 106.

<Front Observation Optical System>

The observation optical system (front image observation device) 200 is disposed to acquire a front image of the eye fundus Ef. The observation optical system 200 includes, for example, an optical scanner which scans the eye fundus two-dimensionally by using the measurement light (for example, an infrared light) emitted from the light source, and a second light receiving element which receives the light reflected on the eye fundus via a confocal aperture arranged at a substantially conjugate position with the eye fundus. The observation optical system 200 has an apparatus configuration of a so-called ophthalmic scanning laser ophthalmoscope (SLO).

The observation optical system 200 may employ a so-called eye fundus camera type. Further, the OCT optical system 100 may also function as the observation optical system 200. That is, the front image may be acquired by using data for forming the tomographic image which is two-dimensionally acquired (for example, an integrated image in a depth direction of a three-dimensional tomographic image, an integrated value of spectral data at each position of XY, brightness data at each position of XY in a constant depth direction, a retinal outer image and the like).

<Ocular Fixation Target Projection Unit>

The ocular fixation target projection unit 300 has an optical system for guiding a viewing direction of the eye E. The projection unit 300 has an ocular fixation target presented to the eye E, and can guide the eye E in multiple directions.

For example, the ocular fixation target projection unit 300 has a visible light source for emitting a visible light, and two-dimensionally changes a presentation position of an ocular target. Accordingly, a viewing direction is changed and consequently an imaging region is changed. For example, if the ocular fixation target is presented from the same direction as that of an optical axis in imaging, a central portion of the eye fundus is set as the imaging region. Further, if the ocular fixation target is presented upward with respect to the optical axis in imaging, an upper portion of the eye fundus is set as the imaging region. That is, the imaging region is changed depending on a position of the ocular target with respect to the optical axis in imaging.

The ocular fixation target projection unit 300 may employ, for example, various configurations such as a configuration where an ocular fixation position is adjusted by a lighting position of LEDs arrayed in a matrix shape, and a configuration where the optical scanner scans the ocular fixation position by using the light emitted from the light source and the ocular fixation position is adjusted by a lighting control of the light source. Further, the ocular fixation target projection unit 300 may be an internal fixation lamp type or an external fixation lamp type.

<Control Unit>

The control unit 70 includes a CPU (processor), a RAM, a ROM and the like. The CPU of the control unit 70 controls the ophthalmic imaging apparatus 10. The RAM temporarily stores various information. The ROM of the control unit 70 stores various programs for controlling operations of the ophthalmic imaging apparatus 10, an initial value and the like.

A non-volatile memory (hereinafter, abbreviated to a memory) 72, an operation unit 74 and a display unit 75 are electrically connected to the control unit 70. The memory 72 is a non-transitory storage medium which can store contents even when a power supply is off. For example, a hard disk drive, a flash ROM, and a USB memory which is detachably attached to the ophthalmic imaging apparatus 10 can be used as the memory 72. An imaging control program for controlling the ophthalmic imaging apparatus 10 to take the front image and the tomographic image is stored in the memory 72. In addition, the memory 72 stores various information relating to the imaging such as the two-dimensional tomographic images, the three-dimensional images, the front images, and information on the imaging position of the tomographic image. Various operation instructions are input to the operation unit 74 by an examiner.

The operation unit 74 outputs a signal corresponding to an input operation instruction to the control unit 70. For example, the operation unit 74 may employ at least any one of a mouse, a joystick, a keyboard, a touch panel and the like. The display unit 75 may be a display mounted on a main body of the ophthalmic imaging apparatus 10 or a display connected to the main body. A display of a personal computer (hereinafter, referred to as a "PC") may be used. Multiple displays may be used simultaneously. The display unit 75 displays various images including the tomographic images and the front images which are taken by the ophthalmic imaging apparatus 10.

The control unit 70 may be configured by multiple control units (that is, multiple processors). For example, the control unit 70 of the ophthalmic imaging apparatus 10 may be configured by a setting control unit disposed in the PC and an operation control unit for controlling the operation of the OCT optical system 100. In this case, for example, the setting control unit of the PC may set the imaging position of the tomographic image based on the operation of the operation unit 74 connected to the PC, and may instruct the set contents to the operation control unit. The operation control unit may control imaging operations performed by each component of the ophthalmic imaging apparatus 10 according to the instruction from the setting control unit. In addition, the process of generating (acquiring) the image based on a light receiving signal may be performed by either the operation control unit or the setting control unit.

For example, the control unit 70 acquires the tomographic image by image processing based on the light receiving signal output from the detector 120 of the OCT optical system 100, and acquires the front image based on the light receiving signal output from the light receiving element of the observation optical system 200. In addition, the control unit 70 controls the ocular fixation target projection unit 300 to change the ocular fixation position.

For example, the control unit 70 controls a display screen of the display unit 75. The acquired image of the eye fundus is output to the display unit 75 as a still image or a moving image, and is stored in the memory 72. The control unit 70 controls each component of the OCT optical system 100, the observation optical system 200 and the ocular fixation target projection unit 300, based on the operation signal output from the operation unit 74.

<Control Operation>

The control operation of the above-described apparatus will be described. An examiner instructs a subject person to gaze at the ocular fixation target of the ocular fixation target projection unit 300. An anterior ocular segment observation image imaged by an anterior ocular segment observation camera (not shown) is displayed on the display unit 75. Then, the examiner performs an alignment operation such that the optical axis in measuring is positioned in the center of the pupil of the anterior ocular segment.

The control unit 70 controls the drive of the optical scanner 108 to scan the eye fundus in a predetermined direction by using the measurement light. The control unit 70 acquires the light receiving signal corresponding to a predetermined scanning area, from an output signal output from the detector 120, thereby forming the tomographic image. In addition, the control unit 70 controls the OCT optical system 100 to acquire the tomographic image, and controls the observation optical system 200 to acquire the front image of the eye fundus. The control unit 70 acquires the tomographic image by using the OCT optical system 100, and acquires the front image of the eye fundus by using the observation optical system 200 at each time.

Figure 2:
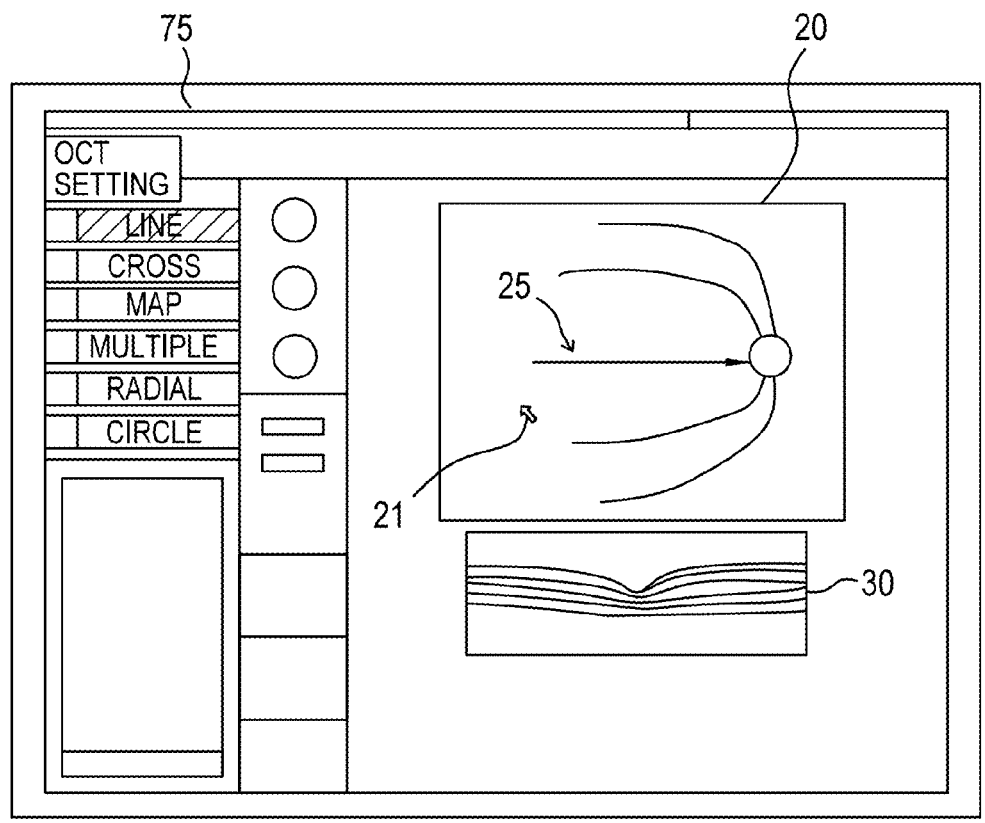
FIG. 2 shows an example of a display screen displayed on a display unit.

FIG. 2 shows an example of a display screen displayed on the display unit 75. The control unit 70 displays a front image 20 acquired by the observation optical system 200, an indicator 25 and a tomographic image 30 on the display unit 75. A scan pattern 25 is an indicator which indicates a measurement position (acquisition position) of the tomographic image on the front image 20. The scan pattern 25 is electrically displayed on the front image displayed on the display unit 75.

The control unit 70 displays a pointer 21 (for example, a cross mark, a dot mark, a pen mark or the like) on the display unit 75. The control unit 70 moves the pointer 21 based on the operation signal from the operation unit 74.

In the present example, in a state where the pointer 21 is placed on the front image 20, the operation unit 74 is operated (for example, a drag operation and a click operation), thereby an imaging condition can be set. The pointer 21 is used in designating an arbitrary position on the display unit 75.

<Setting of Scan Line>

Hereinafter, a case where a line scan pattern is set as the scan pattern will be described as an example. The scan pattern 25 is set in an arbitrary shape in advance based on the operation of the examiner. For example, the scan pattern 25 is selected from multiple prepared scan patterns.

If the tomographic image and the front image are displayed on the same screen, the examiner sets the position of the tomographic image which the examiner desires to image, from the front image displayed on the display unit 75. Here, the examiner performs a moving operation (for example, dragging operation) by using the operation unit 74, thereby moving the scan pattern 25 with respect to the front image 20.

If the scan pattern 25 is moved with respect to the front image 20 by the examiner, the control unit 70 sets the scanning position at each time. Then, the control unit 70 acquires the tomographic image at the scanning position corresponding to the set position. Then, the control unit 70 displays the acquired tomographic image on the display screen of the display unit 75 at each time. The control unit 70 changes the scanning position of the measurement light based on the operation signal output from the operation unit 74, and displays the scan pattern 25 at a display position corresponding to the changed scanning position. That is, the control unit 70 sets the scanning position and consecutively acquires the tomographic image at a certain frame rate, thereby updating the moving image of the tomographic image.

Hereinafter, operations of the present apparatus will be described. After the setting of the measurement position is completed, when an image acquisition start signal (image capture start signal) is input from the operation unit 74, the control unit 70 starts the image acquisition operation of the tomographic image and the front image.

In the present example, in order to acquire one piece of the tomographic image (B scan image) in which noise components are suppressed, a predetermined scanning area is scanned multiple times by using the measurement light to acquire multiple tomographic images, and the acquired multiple tomographic images are averaged through an adding process performed by the control unit 70. In this case, the control unit 70 divides each tomographic image into the same multiple areas in the scanning direction of the measurement light, and acquires information of positional deviation by detecting the positional deviation between the respective tomographic images for each divided area. Then, the control unit 70 corrects the positional deviation between the respective taken images for each divided area, based on the acquired information of the positional deviation. Then, the control unit 70 adds each corrected image to be averaged.

When acquiring the averaged image, the control unit 70 may acquire the averaged image based on the multiple tomographic images, for example, by utilizing an absolute value (A scan signal after forming the image) of a real component and an imaginary component of the depth information for forming the tomographic image. Alternatively, the control unit 70 may acquire the averaged image by utilizing the real and imaginary components in a Z space serving as a basis of each tomographic image. Further, the control unit 70 may acquire the averaged image based on the multiple tomographic images by synthesizing first averaged data with second averaged data after acquiring the first averaged data using the signal of the real component and acquiring the second averaged data using the signal of the imaginary component.

In response to the input of the image acquisition start signal, the control unit 70 controls the OCT optical system 100 to repeatedly acquire the tomographic image at a set frame rate (for example, 10 Hz to 15 Hz (super fine mode)). The frame rate when acquiring the tomographic image may be changed or may not be changed before and after the image acquisition start.

The control unit 70 acquires the multiple tomographic images at the same scanning position. Therefore, the scanning is repeated at substantially the same position on the eye fundus. This multiple time scanning enables the control unit 70 to acquire the multiple tomographic images at substantially the same position.

Specifically, the control unit 70 controls the optical scanner 108 to scan the set scanning position multiple times by using the measurement light. Then, the control unit 70 generates multiple frames (n sheets (n≥2)) of the tomographic images at the same scanning position. The control unit 70 controls the memory 72 to store the multiple generated tomographic images.

On the other hand, in response to the input of the image acquisition start signal, the control unit 70 controls the observation optical system 200 to repeatedly acquire the front image at a set frame rate (for example, 10 Hz to 15 Hz). The frame rate when acquiring the tomographic image may be changed or may not be changed before and after the image acquisition start. The frame rate when acquiring the tomographic image and the frame rate when acquiring the front image may be the same frame rate or may be different frame rates. In addition, acquisition operations of the tomographic image and the front image may be synchronized with each other or may be asynchronous.

The control unit 70 repeats an acquisition operation of the front image while the multiple tomographic images are acquired. According to this control, the control unit 70 monitors the movement of the eye E while the tomographic image is consecutively acquired.

Specifically, the control unit 70 controls the observation optical system 200 to receive the reflection light from the front surface of the eye fundus Ef. The control unit 70 processes the received reflection light, thereby generating the multiple frames of the front images. The control unit 70 controls the memory 72 to store the multiple generated front images. As described above, the control unit 70 controls the generation of the front image to be performed in parallel with the generation of the tomographic image.

<Determination of Tomographic Image Using Front Image>

Figure 3:
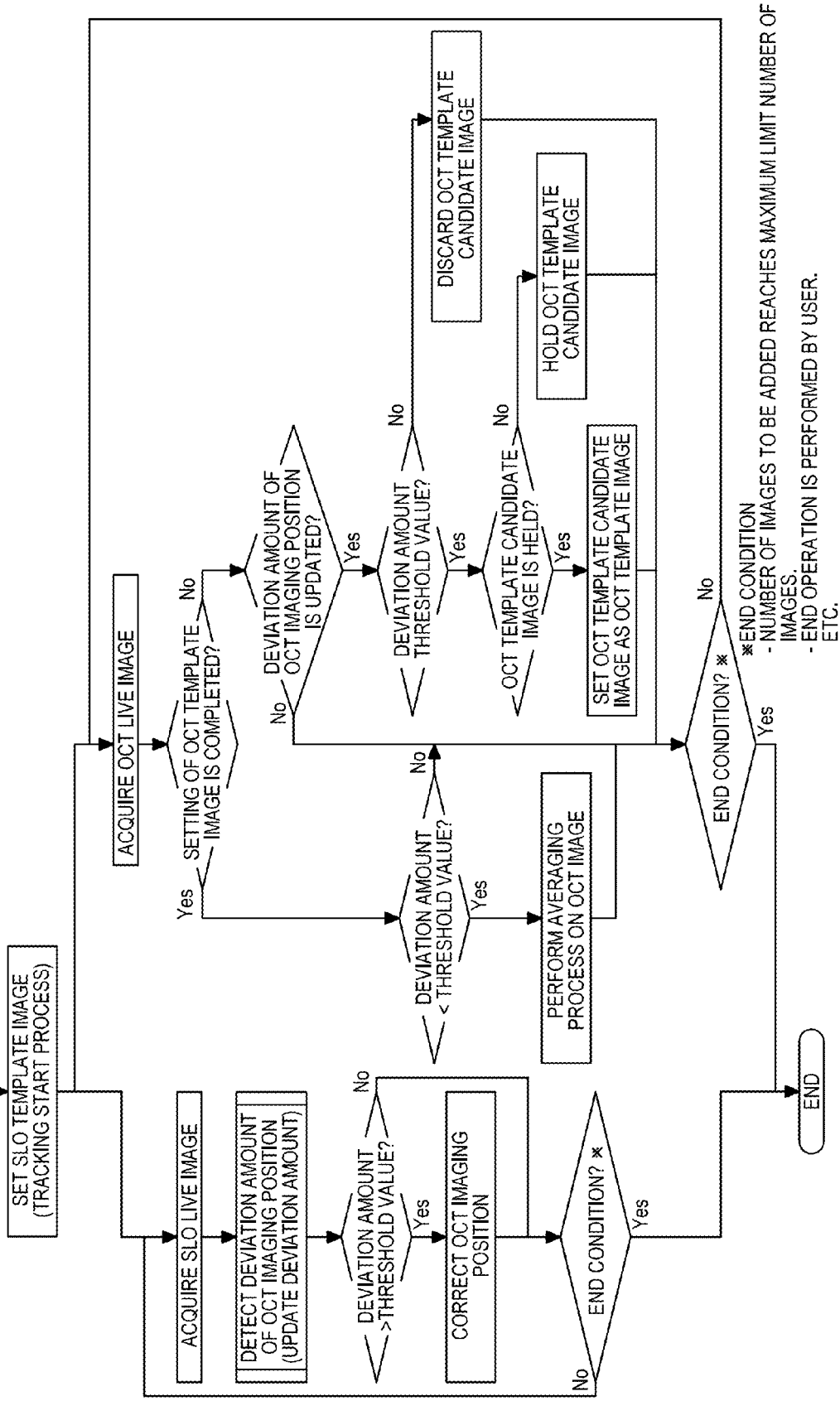
FIG. 3 is a flowchart showing an exemplary determination method for determining appropriateness of whether a tomographic image is acquired at a position set in advance.

FIG. 3 is a flowchart showing an exemplary determination method for determining appropriateness of whether the acquired tomographic image is acquired at a position set in advance. The determination is made in real time. The determination result is used in setting an OCT template image of the tomographic image (first reference image) when performing an averaging process.

The control unit 70 first sets a template image of the front image (second reference image) for detecting the positional deviation of the front image. As the second reference image, the front image acquired when the image acquisition start signal is input may be used.

The control unit 70 acquires a live image of the front image. The control unit 70 performs image processing to calculate the positional deviation between the second reference image and the live front image which is repeatedly generated. Accordingly, a deviation amount D1 of the imaging position of the OCT is detected in real time. The deviation amount D1 is updated at the time when a deviation amount between the front image and the second reference image is newly detected.

The control unit 70 determines whether the deviation amount D1 satisfies a permissible range (for example, a predetermined threshold value). Here, each time one frame of the front image is acquired, the control unit 70 determines whether the deviation amount D1 with respect to the second reference image satisfies the permissible range. That is, the control unit 70 acquires the determination result in real time, for each front image which is consecutively acquired.

Then, when the deviation amount D1 does not satisfy the permissible range (for example, a predetermined threshold value), the control unit 70 controls the optical scanner 108 to correct the imaging position of the OCT. For example, the control unit 70 appropriately controls the drive of two galvanometer mirrors of the optical scanner 108 so that the deviation of the scanning position is corrected. Since this corrects the scanning position, the imaging position is corrected (tracking control).

The above-described operation is repeatedly performed until the number of added images reaches the maximum number of images or until the examiner performs the completion operation.

Next, an operation performed when setting the OCT template image (first reference image) will be described. The control unit 70 acquires the live image of the tomographic image in parallel with the acquisition of the live image of the front image. Then, the control unit 70 determines whether the OCT template image is set.

When the OCT template image is not set, the control unit 70 determines whether the deviation amount of the imaging position of the OCT is updated. When not updated, the process returns to the acquisition of the live image of the OCT.

When updated, the control unit 70 determines whether the above-described deviation amount D1 satisfies the permissible range (for example, a predetermined threshold value). When the deviation amount D1 does not satisfy the permissible range, the control unit 70 discards the live image of the acquired tomographic image (OCT template candidate image). Then, the process returns to the acquisition operation for the live image of the OCT. In contrast, when the deviation amount D1 satisfies the permissible range, the process proceeds to the next step.

In the next step, the control unit 70 determines whether the OCT template candidate image is held. In a case of No, the control unit 70 holds the live image of the acquired tomographic image as the OCT template candidate image. In a case of Yes, the control unit 70 sets the OCT template candidate image held in advance to be the OCT template image.

When the OCT template image is set in the above-described manner, the control unit 70 determines whether the above-described deviation amount D1 satisfies the permissible range. In a case of No, the live image of the acquired tomographic image is discarded or ignored, and the process returns to the acquisition of the tomographic image. In a case of Yes, the control unit 70 uses the acquired tomographic image and the OCT template image to perform the averaging process. The above-described operation is repeatedly performed until the number of added images reaches the maximum number of images or until the examiner performs an end operation.

In the operation until the OCT template image is set in the above-described flowchart, if the determination that the deviation amount D1 satisfies the permissible range is made for the first time, the acquired tomographic image is held as the OCT template candidate image. Thereafter, if the determination that the deviation amount D1 satisfies the permissible range is consecutively made for the second time, the acquired tomographic image is held as the OCT template candidate image. In contrast, if the determination that the deviation amount D1 satisfies the permissible range is not consecutively made, the OCT template candidate image held by the first time determination is discarded.

That is, the control unit 70 determines appropriateness of the tomographic image by utilizing the consecutiveness of the determination result with respect to the front image. Then, the control unit 70 sets the reference image (first reference image) of the tomographic image acquired when performing the averaging process, based on the determination result of the appropriateness.

Specifically, the control unit 70 determines the tomographic image acquired when the front images satisfying the permissible range are consecutive, as appropriate, and determines the tomographic image acquired when the front images satisfying the permissible range are not consecutive, as inappropriate. Then, the control unit 70 takes the tomographic image determined as appropriate as the reference image, and synthesizes the reference image with the other tomographic image to generate the averaged image.

Figure 4:
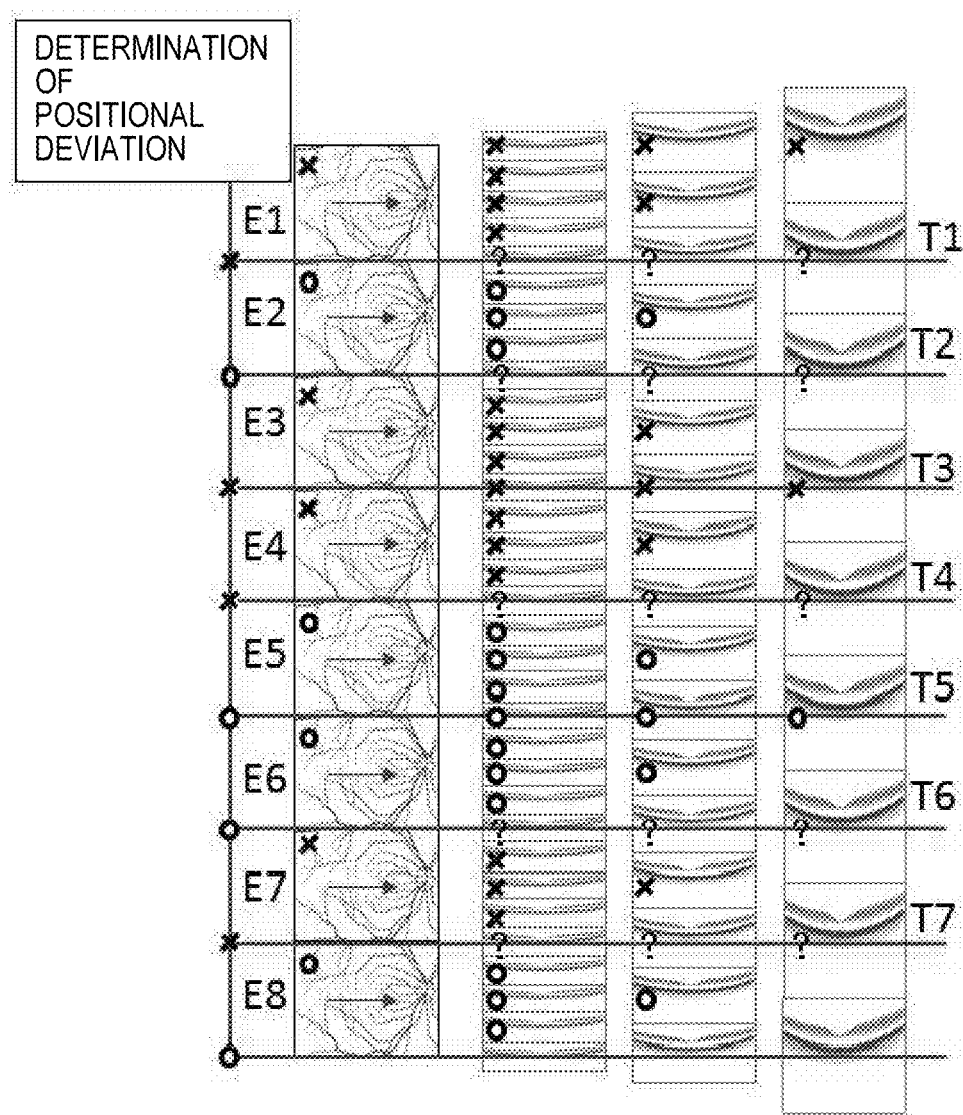
FIG. 4 shows an example of determination when using consecutiveness of determination results with respect to a front image.

FIG. 4 shows an example of determination when using the consecutiveness of the determination result with respect to the front image. FIG. 4 shows a case where the tomographic image and the front image are asynchronously acquired.

For example, regarding a front image E1 of the first sheet and a front image E2 of the second sheet which are consecutive in the acquisition order, the front image E2 satisfies the permissible range, but the front image E1 does not satisfy the permissible range. Therefore, a tomographic image T1 acquired while acquiring the front image E1 and the front image E2 is determined as inappropriate. Similarly, regarding the front image E2 and a front image E3, since the front image E3 does not satisfy the permissible range, a tomographic image T2 is determined as inappropriate. In addition, regarding the front image E3 and a front image E4, since both front images do not satisfy the permissible range, a tomographic image T3 is determined as inappropriate. Further, regarding the front image E4 and a front image E5, since the front image E4 does not satisfy the permissible range, a tomographic image T4 is determined as inappropriate.

Regarding the front image E5 and a front image E6, the control unit 70 determines that both front images satisfy the permissible range, that is, that the front images satisfying the permissible range are consecutive. Therefore, a tomographic image T5 acquired while acquiring the front image E5 and the front image E6 is determined as appropriate. The control unit 70 controls the memory 74 to store the tomographic image T5 as the template image (first reference image) of the tomographic image for performing the averaging process.

The control unit 70 distinguishes the tomographic image acquired while acquiring multiple front images (which are consecutive in the acquisition order). For example, the control unit 70 may output respective time signals when the generation of the respective front images is completed (output time stamps). Here, the control unit 70 outputs a first time signal when the generation of a first front image is completed. The control unit 70 outputs a second time signal when the subsequent generation of a second front image is completed. The control unit 70 takes the tomographic image generated during a time interval from when the first time signal is output until the second time signal is output, as the tomographic image acquired while acquiring the first front image and the second front image. While acquiring multiple front images, if multiple tomographic images are acquired, the control unit 70 controls the memory 72 to collectively store the tomographic images.

Next, a process after the template image is acquired will be described in detail. After the template image of the tomographic image is acquired, if the subsequent tomographic image is acquired, the control unit 70 synthesizes these tomographic images through image processing, thereby acquiring averaged data. The acquired averaged data is stored in the memory 74. The averaged data may be an averaged image itself, or may be brightness information serving as a basis of the averaged image (brightness information to which brightness of each image is added). When synthesizing the images, it is preferable that the control unit 70 perform alignment between the tomographic images through image processing (for example, with regard to the alignment method, refer to JP-A-2010-110392).

For example, the control unit 70 repeatedly acquires the tomographic image and the front image until the number of the tomographic images to be added reaches a predetermined number of images. Furthermore, each time the tomographic image is added, the control unit 70 synthesizes the averaged data which is added in advance with the added tomographic image, thereby updating the averaged data. The updated synthesized data is stored in the memory 74.

In the flowchart of FIG. 3, the control unit 70 utilizes the deviation amount D1 to determine the appropriateness of the tomographic image used in an addition process. Then, the control unit 70 uses the tomographic image for which it is determined that the deviation amount D1 is within the permissible range, in the addition process to the template image. The control unit 70 does not use the tomographic image which is determined that the deviation amount D1 does not satisfy the permissible range, in the addition process to the reference image. When determining the appropriateness of the tomographic image used in the addition process to the reference image, the positional deviation or correlation between the tomographic images may be used.

When the number of the tomographic images to be added reaches a predetermined number of images, the control unit 70 completes the image acquisition operation. Then, the control unit 70 generates the averaged image of the tomographic images based on the averaged data stored in the memory 74. The control unit 70 displays the generated averaged image on the display unit 75. In addition, the control unit 70 causes the memory 74 to store the generated averaged image.

As described above, the tomographic image acquired when the front images satisfying the permissible range are consecutive is set as the reference image. Accordingly, the tomographic image which has a high possibility of being acquired at the same position as the scanning position set in advance is set as the reference image. Therefore, it is possible to smoothly acquire the averaged image with high precision.

If attempting to determine appropriateness of the tomographic image by using the positional deviation of only one front image, even if the eye E is moved during the acquisition of the front image, there is a case where the tomographic image is determined as appropriate. For example, when determining the appropriateness of the tomographic image acquired after generating one front image, there is a possibility that the eye E may be moved at the time when the tomographic image is generated. As a result, in some cases, the tomographic image having the positional deviation may be set as the reference image. In this case, since the acquisition position of the tomographic image is different from the position set in advance, it is difficult to generate an appropriate averaged image. Therefore, the consecutiveness is determined as described above. According to the configuration of this example, even when the eye E is moved after acquiring one front image, it is possible to determine that the subsequent front image does not satisfy the permissible range, thereby enabling the above-described problem to be overcome.

Modified Example

Consecutiveness of Front Image

In the above description, the control unit 70 determines that, in the front images which are consecutive for one time in the acquisition order, the tomographic image acquired when the front images satisfying the permissible range are consecutive for two times is appropriate, and determines that the tomographic image acquired when the front image satisfying the permissible range is not consecutive is inappropriate. However, the control unit 70 may use the front images which are consecutive for two time or more in the acquisition order. For example, the control unit 70 may determine that the tomographic image acquired when the front images satisfying the permissible range are consecutive for two times is appropriate, and may determine that the tomographic image acquired when the front image is consecutive for one time or when the front image satisfying the permissible range is not consecutive is inappropriate. In this case, the control unit 70 may select the tomographic image acquired when the front image at the center of the series of front images satisfying the consecutiveness of the positional deviation is acquired.

The present example is not limited to a configuration (refer to the rightmost side column of the tomographic image in FIG. 4) where the tomographic image is acquired once while the front image is acquired twice. For example, the technology of the present example can be applied to a configuration (refer to the leftmost side column and the middle column of the tomographic image in FIG. 4) where the tomographic image is acquired multiple times while the front image is acquired twice.

<Observation Optical System>

In the above description, the SLO optical system is used as the observation optical system 200, but the present example is not limited thereto. That is, the observation optical system 200 may be any front view observation optical system can acquire the front image of the subject eye E. For example, the observation optical system 200 may employ a configuration where the eye fundus Ef of the subject eye E is imaged by an infrared camera. The infrared camera generally has a frame rate which is faster than that of the SLO optical system. Accordingly, the consecutiveness can be determined in a shorter time period, thereby enabling the determination of the tomographic image to be performed in a short time period. On the other hand, when using the SLO optical system, even in the SLO optical system whose frame rate is slow, there is an advantage in that it is possible to properly determine the appropriateness of the tomographic image by determining the above-described consecutiveness.

The observation optical system 200 may be an anterior ocular segment observation optical system which observes an anterior ocular segment image of the subject eye E. That is, when acquiring the tomographic image of the eye fundus Ef of the subject eye E, the tomographic image may be selected by determining the consecutiveness of the positional deviation of the anterior ocular segment image acquired by the anterior ocular segment observation optical system.

<Association of Acquisition Time for Front Image and Tomographic Image>

In the above description, the acquisition time of the front image is associated with the acquisition time of the tomographic image by using the time signal acquired at the time when the generation of each front image is completed. However, the present example is not limited thereto.

That is, the control unit 70 may use at least some control information of the OCT optical system 100 and the observation optical system 200. For example, the scanning position when acquiring the front image and the tomographic image may be used.

The control unit 70 detects the scanning position of the optical scanner 108 and the scanning position of the optical scanner of the observation optical system 200. Then, the control unit 70 outputs the time signal indicating the start and the end of optical scanning for acquiring each front image. Here, the control unit 70 outputs a first time signal when the scanning position in the observation optical system 200 reaches the start position for acquiring each front image. The control unit 70 outputs a second time signal when the scanning position in the observation optical system 200 reaches the end position for acquiring each front image.

On the other hand, the control unit 70 outputs a time signal when the scanning position of the optical scanner 108 reaches the start position and the end position for acquiring each tomographic image.

Then, the control unit 70 uses the scanning position of the optical scanner 108 to specify the tomographic image acquired during a time interval T2 which is a time period from when the first time signal is output in the first front image to when the second time signal is output in the subsequent second front image. That is, the tomographic image on which the optical scanning is performed from the start position to the end position during the time interval T2 may be taken as the tomographic image acquired during the acquisition of the first front image and the second front image.

<Application of Synthesized Image Other than Averaged Image>

In the above description, the consecutiveness of the determination result with respect to the front image is used in order to acquire the averaged image in the tomographic image, but the present example is not limited thereto. That is, the present example may employ a configuration of determining the appropriateness of the tomographic image used in synthesizing the images by utilizing the consecutiveness of the determination result with respect to the front image. For example, based on the determination result of the appropriateness, the control unit 70 sets the template image (first reference image) of the tomographic image acquired when the image synthesizing process is performed. The control unit 70 determines that the tomographic image acquired when the front images satisfying the permissible range are consecutive is appropriate, and determines that the tomographic image acquired when the front image satisfying the permissible range is not consecutive is inappropriate. Then, the control unit 70 takes the tomographic image determined to be appropriate as the reference image, and acquires the synthesized image by synthesizing the reference image with the other tomographic image. The image synthesizing process, for example, may include a super-resolution image processing (for example, refer to JP-A-2013-034658), a noise removal processing and the like.

<Application to Cases Other than Case where Multiple Tomographic Images are Acquired at Same Position>

In the above description, a case has been described where the subject eye E is scanned multiple times at the same scanning position, but the present example is not limited thereto. For example, the present example can be applied even to a case where the scanning position on the subject eye E is changed and the tomographic images are acquired by using the multiple different scanning lines.

The scan pattern for acquiring the tomographic images by using the multiple different scanning lines may include, for example, a scan where the scanning lines in the same direction are formed at the different positions, a cross scan, a raster scan, a radial scan and the like. The cross scan has, for example, a scan pattern where the multiple scanning lines intersect each other. The raster scan has, for example, a scan pattern where raster is performed inside a rectangle by using the measurement light. The radial scan has, for example, a scan pattern where multiple scanning lines are radially arrayed.

For example, as the multiple different scanning lines, the first scanning line and the second scanning line are set. The control unit 70 sets the front image acquired when the acquisition start signal is issued, as the second reference image. The control unit 70 may set the front image acquired when the tomographic image is acquired in the first scanning line, as the second reference image.

The control unit 70 calculates, through image processing, the positional deviation between the template image (hereinafter, referred to as a second reference image) of the front image and the front image acquired when the tomographic image is acquired in the second scanning line. Each time one frame of the front image is acquired, the control unit 70 determines whether the positional deviation amount with respect to the second reference image satisfies the permissible range. That is, the control unit 70 acquires the determination result for each front image which is consecutively acquired, in real time.

Here, the control unit 70 determines the appropriateness of the tomographic image acquired in the second scanning line, by utilizing the consecutiveness of the determination result with respect to the front image. When the tomographic image is acquired in the second scanning line, the control unit 70 determines that the tomographic image acquired when the front images satisfying the permissible range are consecutive is appropriate, and determines that the tomographic image acquired when the front image satisfying the permissible range is not consecutive is inappropriate. Then, the control unit 70 causes the memory 72 to store the tomographic image determined to be appropriate as the tomographic image acquired in the second scanning line.

Thereafter, when a third scanning line is set, the control unit 70 may move the process from the second scanning line to the third scanning line. The subsequent process is the same as the process in the second scanning line. Accordingly, the description thereof will not be repeated.

The tomographic image acquired in each scanning line is associated with the set scan pattern. The associated tomographic image data is used in output to a monitor 74, analysis of the subject eye or the like.

As described above, even when the tomographic images are acquired at the different scanning positions, the tomographic image can be acquired which has a high possibility of being acquired at the same position as the scanning position set in advance. That is, it is possible to reliably acquire the tomographic image in each scanning line.

In the above description, the moving image of the tomographic image and the moving image of the front image are simultaneously acquired. However, the present example is not limited thereto. For example, the concept of the present example can be applied to a configuration where the moving image of the tomographic image and the moving image of the front image are alternately acquired on a frame by frame.

What is claimed is:

1. An ophthalmic imaging apparatus comprising:
   an optical coherence tomography (OCT) optical system configured to acquire a tomographic image of a subject eye by using interference between a measurement light which is emitted to the subject eye and a reference light;
   an observation optical system configured to acquire a front image of the subject eye;
   a processor; and
   a memory storing computer readable instructions, when executed by the processor, causing the ophthalmic imaging apparatus to function as:
      an image generation unit configured to repeatedly generate the tomographic image based on an output signal from the OCT optical system, and repeatedly generate the front image based on an output signal from the observation optical system;
      a determination unit configured to detect a positional deviation between a front image set as a reference front image and each of front images generated by the image generation unit, and to determine consecutiveness of the front images whose positional deviation satisfies a permissible range; and
      a selection process unit configured to perform selection process to select one of multiple tomographic images generated by the image generation unit, based on a determination result by the determination unit.

2. The ophthalmic imaging apparatus according to claim 1, wherein the memory further stores computer readable instructions, when executed by the processor, causing the ophthalmic imaging apparatus to function as an image synthesis unit configured to synthesize multiple tomographic images generated by the image generation unit,
   wherein the selection process unit is configured to select a reference tomographic image to be synthesized by the image synthesis unit, from the multiple tomographic images generated by the image generation unit, based on the determination result by the determination unit, and
   wherein the image synthesis unit is configured to synthesize the reference tomographic image selected by the selection process unit and at least one tomographic image acquired at a time different from an acquisition time of the reference tomographic image.

3. The ophthalmic imaging apparatus according to claim 1, wherein the OCT optical system includes an optical scanner configured to scan the subject eye by using the measurement light emitted to the subject eye,
   wherein the memory further stores computer readable instructions, when executed by the processor, causing the ophthalmic imaging apparatus to function as a scanning control unit configured to control a drive of the optical scanner to scan a same pre-set scanning position multiple times by using the measurement light, and
   wherein the selection process unit is configured to select a tomographic image corresponding to the scanning position based on the determination result by the determination unit.

4. The ophthalmic imaging apparatus according to claim 1, wherein the OCT optical system includes an optical scanner configured to scan the subject eye by using the measurement light emitted to the subject eye,
   wherein the memory further stores computer readable instructions, when executed by the processor, causing the ophthalmic imaging apparatus to function as a scanning control unit configured to control a drive of the optical scanner to sequentially scan multiple scanning positions by using the measurement light, the multiple scanning position being set by a scan pattern formed from multiple scanning lines, and
   wherein the selection process unit is configured to select a tomographic image corresponding to the scanning positions based on the determination result by the determination unit.

5. The ophthalmic imaging apparatus according to claim 1, wherein the determination unit is configured to determine whether the front images whose positional deviation satisfy the permissible range are consecutive for three or more times.

6. The ophthalmic imaging apparatus according to claim 1, wherein the selection process unit is configured to select the tomographic image acquired while acquiring a series of the front images which are determined to be consecutive by the determination unit.

7. The ophthalmic imaging apparatus according to claim 6, wherein the memory further stores computer readable instructions, when executed by the processor, causing the ophthalmic imaging apparatus to function as a specifying process unit configured to specify the tomographic image acquired while acquiring the series of the front images, by using a time when the image generation device unit generates each of the front images.

8. The ophthalmic imaging apparatus according to claim 6, wherein the memory further stores computer readable instructions, when executed by the processor, causing the ophthalmic imaging apparatus to function as a specifying process unit configured to specify the tomographic image acquired while acquiring the series of the front images, based on control information when the OCT optical system or the observation optical system is controlled.

9. The ophthalmic imaging apparatus according to claim 1,
wherein the determination unit is configured to determine whether at least two consecutively acquired front images satisfy the permissible range, and
wherein the selection process unit is configured to select the tomographic image acquired while acquiring the at least two front images which are determined to satisfy the permissible range.

10. An ophthalmic imaging apparatus comprising:
an OCT optical system configured to acquire a tomographic image of a subject eye by using interference between a measurement light which is emitted to the subject eye and a reference light;
an observation optical system configured to acquire a front image of the subject eye; and
a controller configured to:
  repeatedly generate the tomographic image based on an output signal from the OCT optical system, and repeatedly generate the front image based on an output signal from the observation optical system;
  detect a positional deviation of each of multiple front images with respect to a front image set as a reference front image, the multiple front images being consecutive in an acquisition order;
  select, as a reference tomographic image, a tomographic image acquired when the detected positional deviation consecutively satisfies a permissible range, and not select, as the reference tomographic image, a tomographic image acquired when the detected positional deviation does not satisfy the permissible range or when the positional deviation satisfying the permissible range is not consecutive; and
  synthesize the selected reference tomographic image and a tomographic image acquired at a time different from an acquisition time of the reference tomographic image.

* * * * *